(12) United States Patent  
Gueller et al.

(10) Patent No.: US 7,931,869 B2  
(45) Date of Patent: Apr. 26, 2011

(54) DEVICE FOR DOSAGE OF SUBSTANCES

(75) Inventors: Rolf Gueller, Herznach (CH); Michael Schneider, Frick (CH); Josef Schroer, Muttenz (CH); Christoph Moor, Kuttigen (CH)

(73) Assignee: Chemspeed Technologies AG, Augst (CH)

( * ) Notice: Subject to any disclaimer, the term of this patent is extended or adjusted under 35 U.S.C. 154(b) by 1300 days.

(21) Appl. No.: 10/514,401

(22) PCT Filed: May 13, 2003

(86) PCT No.: PCT/CH03/00305  
§ 371 (c)(1),  
(2), (4) Date: Nov. 15, 2004

(87) PCT Pub. No.: WO03/098170  
PCT Pub. Date: Nov. 27, 2003

(65) Prior Publication Data  
US 2005/0177134 A1    Aug. 11, 2005

(30) Foreign Application Priority Data

May 17, 2002    (CH) ........................................ 846/02

(51) Int. Cl.  
*G01N 21/00*    (2006.01)

(52) U.S. Cl. .......... 422/100; 422/99; 436/180; 222/420; 347/100

(58) Field of Classification Search ............ 422/99–100; 436/180; 222/420; 347/100  
See application file for complete search history.

(56) References Cited

U.S. PATENT DOCUMENTS

| 4,368,684 | A | * | 1/1983 | Launay | 118/25 |
| 5,402,834 | A | * | 4/1995 | Levin et al. | 141/83 |
| 2002/0084290 | A1 | * | 7/2002 | Materna | 222/420 |

FOREIGN PATENT DOCUMENTS

| EP | 0 616 276 A1 | 9/1994 |
| EP | 0 731 344 A1 | 9/1996 |
| WO | WO 02/04900 A1 | 1/2002 |
| WO | WO 02/29369 A1 | 4/2002 |

* cited by examiner

Primary Examiner — Jyoti Nagpaul  
(74) Attorney, Agent, or Firm — Husch Blackwell LLP

(57) ABSTRACT

A device for dosage of substances having a substance intake portion, which included at least one substance compartment for the intake of substance to be dosed, an emptying portion for the emptying the substance compartment and a weighing balance for the determination of the quantity of dosed substance, wherein the substance intake portion includes a plurality of substance compartments, which are able to be individually emptied. The device further includes a control means, which control the emptying of the substance compartments in a manner dependent on the quantity of dosed substance, which is determined by means of the weighing balance.

35 Claims, 8 Drawing Sheets

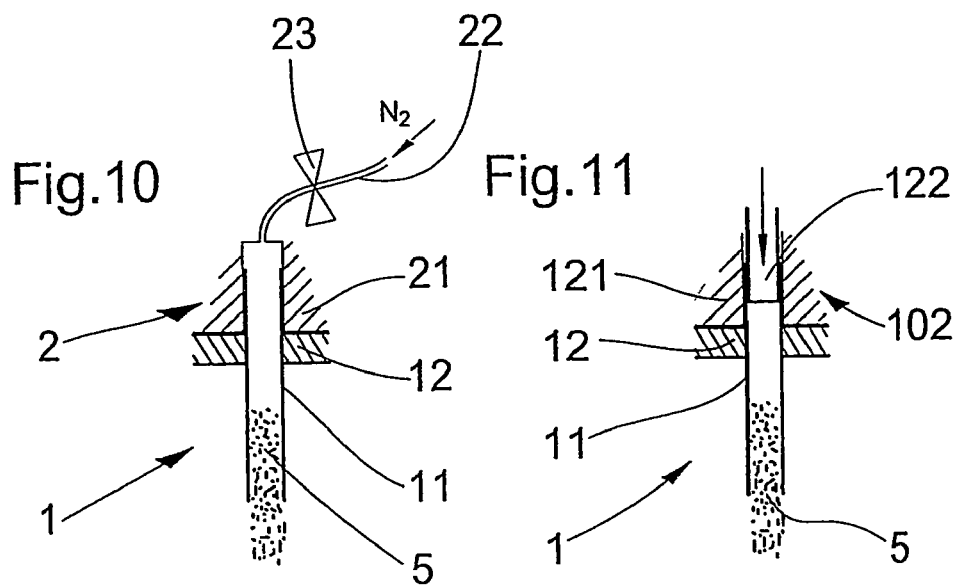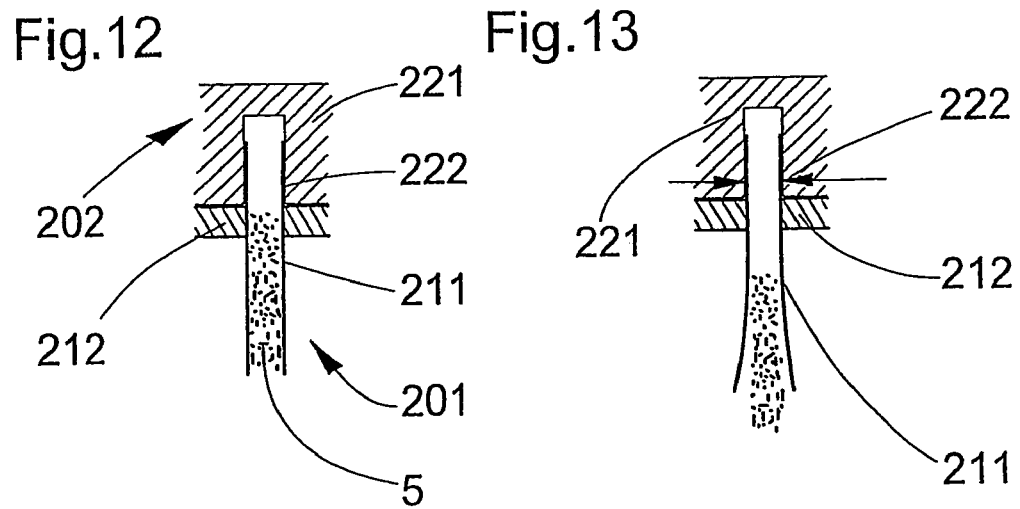

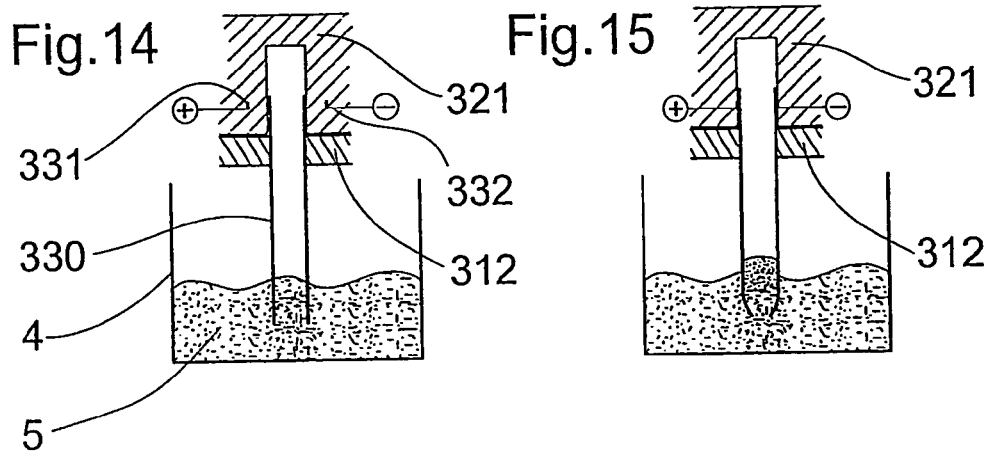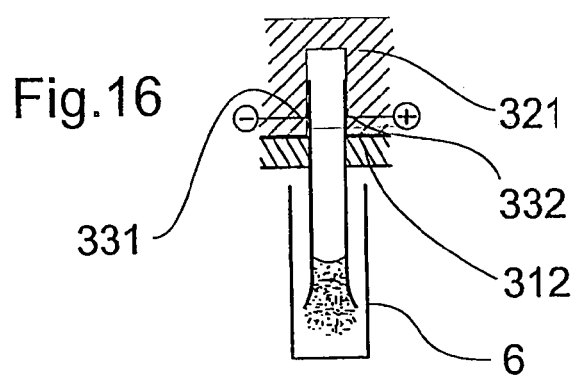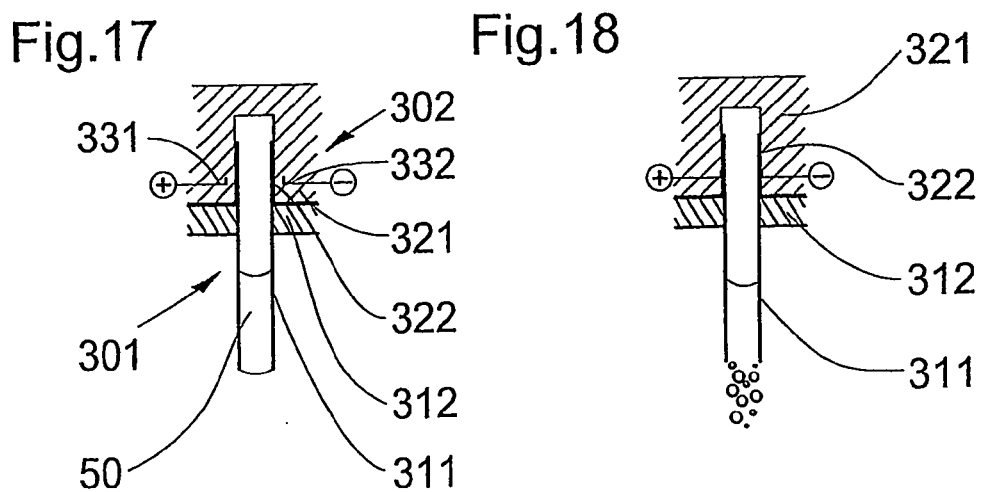

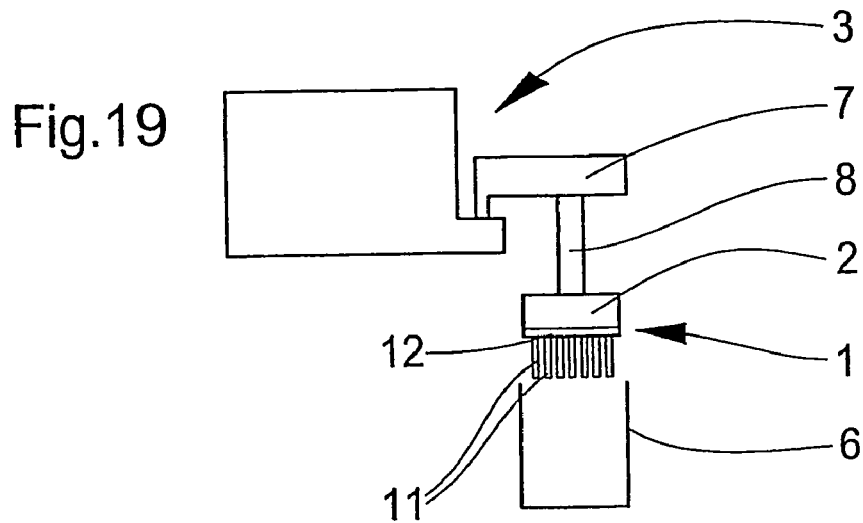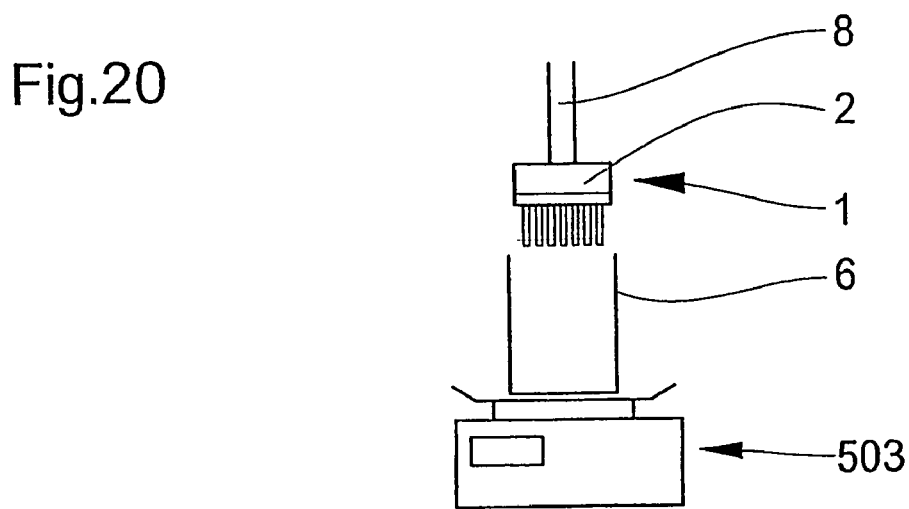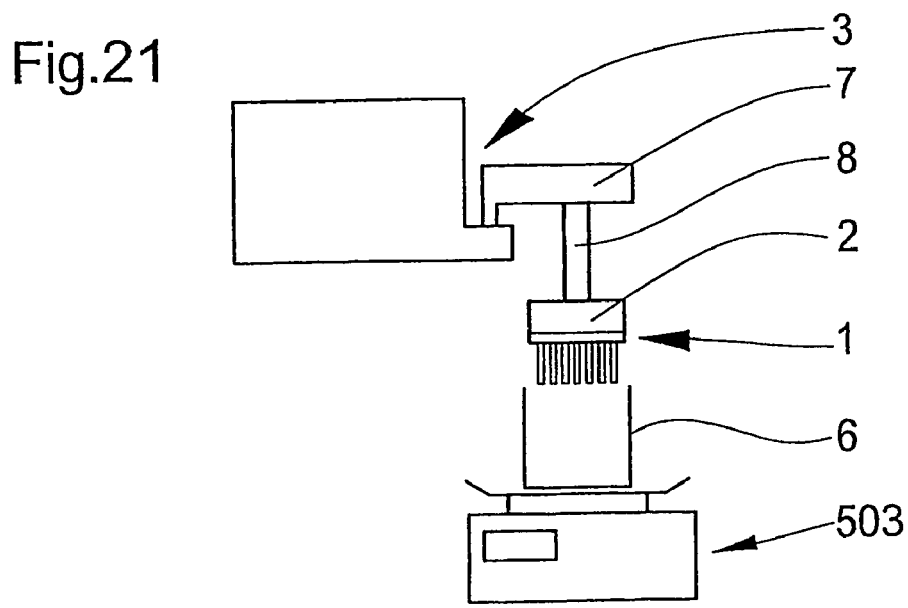

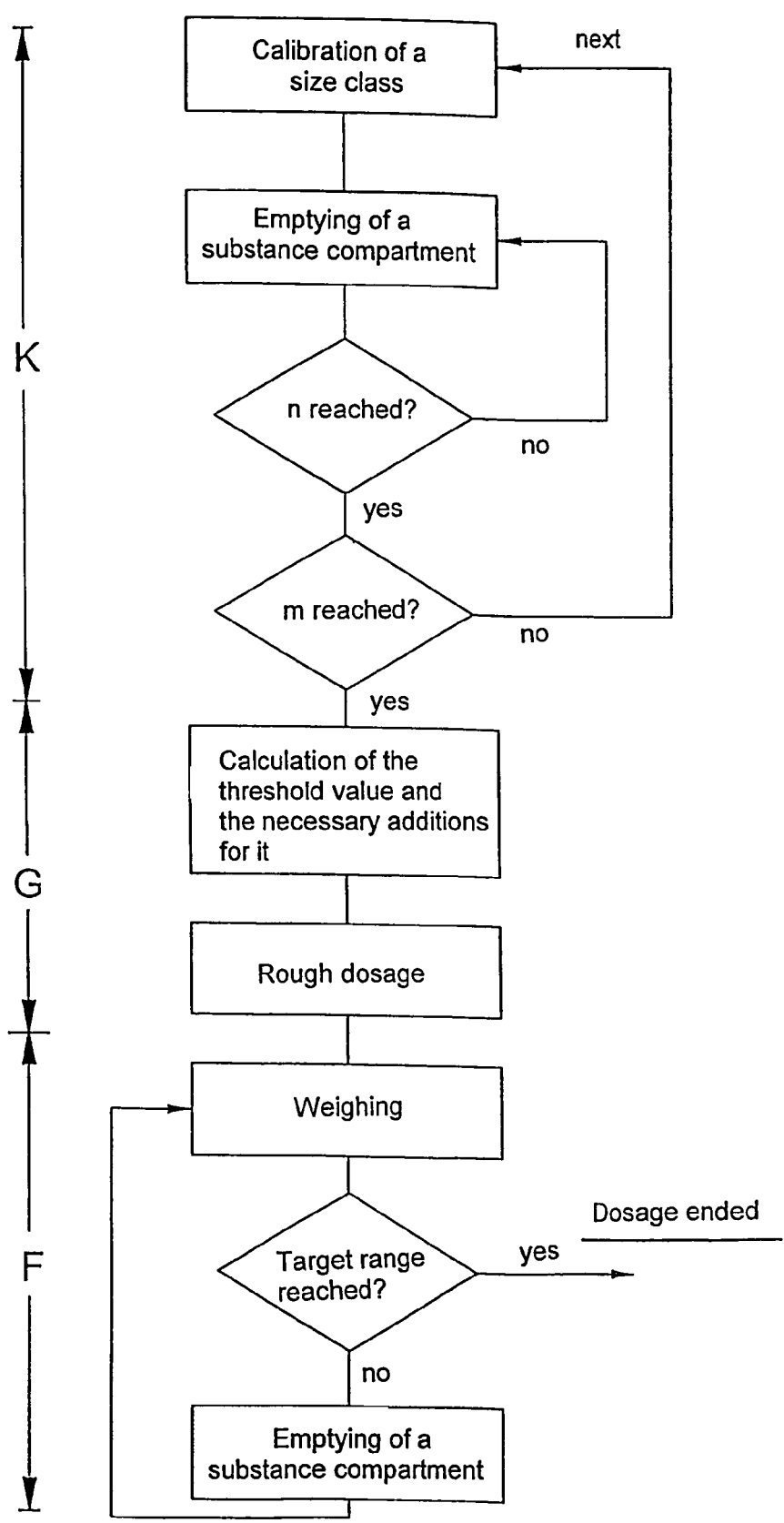

DEVICE FOR DOSAGE OF SUBSTANCES

FIELD OF THE INVENTION

The present invention relates to a device and a method for dosage of substances.

BACKGROUND

In many cases in the laboratory the dosage of substances takes place in containers by manual addition with a spatula into the container to be filled, or into an intermediate container, which is subsequently emptied into the container to be filled, wherein the container or intermediate container is placed on a weighing balance. The achievable precision is limited thereby by the ability of the experimenter. These actions can only be automated with great technical effort. In addition the overdosages which frequently occur are only laboriously manually corrected and when automated, with still greater effort. Moreover, not every container can be placed on a weighing balance, and even if this is possible, one can not dose independent of the location.

For these reasons a dosing device, disclosed in WO 02/29369 A1, was developed by the firm Chemspeed Ltd., CH-4302 Augst, which enables a continuous dosage, which is gravimetrically controlled from above, into any container in any location within the operating capacity of a robotic arm. However in this case the dosing device has to be adjusted to the substance to be dosed and/or the substance has to fulfill certain requirements concerning flowability or the flow behaviour, in order to be able to be continuously dosed.

SUMMARY

In view of the disadvantages of the previously known devices and methods described above, the invention is based on the following object: to provide a device and a method for dosage of substances of the type mentioned at the outset, which for substances which vary in regards to consistency, reactivity, morphology etc., enable an exact, simple and automatable dosing of a desired quantity of substance.

This object is achieved through the device according to the invention and the method according to the invention. Preferred embodiments are found in the dependent claims.

The essence of the invention consists of the following: a device for dosage of substances has a substance intake portion, which comprises a plurality of substance compartments for the intake of substance to be dosed, which are individually emptiable. The device comprises in addition an emptying portion for the emptying of the substance compartments, a weighing balance for the determination of the quantity of dosed substance and control means which control the emptying of the substance compartments in a manner dependent on the quantity of dosed substance, which is determined by means of the weighing balance.

Since the substance intake portion has a plurality of substance compartments, which are individually emptiable, and that a weighing balance is used for the determination of the quantity of dosed substance, diverse substances can be progressively precisely dosed with high speed by means of an approximation technique. The substances are, for example, in fluid, powdery or solid form or they can also be an arbitrary mixture of solid or fluid substances and be of diverse consistencies. The approximation technique can be automated without problem. In addition, dosage can very simply take place from many supply containers into many target vessels. In addition, at least then the dosage is not bound to a location, if a weighing balance is used, which measures from above the weight of the substance intake portion, the emptying portion and the substance present in the substance compartments.

The control means comprises for example a calculator unit with a processor and electrical circuits for the weighing balance and for the emptying portion.

In the case of an advantageous embodiment, the substance intake portion comprises substance compartments of various size classes, with which various quantities of substance to be dosed can be intaken. This enables a rapider approximation of the desired dosage quantity, since firstly a rough approximation can be carried out with larger substance compartments, which can then be refined by the emptying of smaller substance compartments. Additionally a large range can be covered by the various size classes and yet still be dosed with high resolution.

Preferably at least some of the size classes are graduated across at least a factor of 5, for example in the ratio 1:2:5. With an advantageous alternative the size classes are graduated across a factor of 9, for example in the ratio 1:3:9. Since a processor normally undertakes the computations necessary for the dosage, optionally also non-integer ratios are usable, which can for example result from the production of the substance compartments.

With an advantageous embodiment at least some of the substance compartments are pre-filled with substance to be dosed and preferably are sealed. The substance compartments can for example be purchased pre-filled and/or stored pre-filled and then if required be received by the device according to the invention and be emptied. The seal can for example consist of a foil, which is peeled off as a whole directly before use or, alternatively to that, opened by a pressure surge used for the emptying of the substance compartment or another physical or chemical process, in such a way that it advantageously rips so that no remains of the foil fall in the vessels to be filled. E.g. it is also possible on a carrier plate to first fill up various substance compartments with various substances, wherein these can have various physical and chemical properties.

With advantage the substance compartments are formed by vertically arranged tubes. These tubes are for example cylindrical and made from glass, plastic or metal. To take in substance they are preferably dipped in or inserted in the substance and then taken out again. This can be simply automated, it needs only a piece of equipment for vertical displacement of the substance compartments or of the supply container containing the substance.

Preferably the tubes of different size classes have different inner diameters. In the case of dipping or inserting the tubes in the substance and subsequent removal of the tubes, with sufficiently small inner diameters, different substance quantities then adhere in the tubes of different size classes.

Advantageously the inner diameters of the tubes are smaller than 5 mm, preferably smaller than 1 mm, more preferably smaller than 0.5 mm, in particular preferably smaller than 0.1 mm. Thus it is guaranteed that also very fine powdery substances, as well as fluid substances, can be intaken by the tubes.

Preferably at least some of the tubes narrow from the top to the bottom. Thus more space is available on the top for the emptying portion or the taking in of substance.

In the case of an advantageous embodiment, at least some of the tubes have pointed or sharp-edged lower sections. This enables a simpler insertion in powdery or solid substances and with fluid substances leads to a more regular release of drops, i.e. to a more uniform fill level of tubes of the same size class.

In the case of an advantageous embodiment, at least some of the tubes are pre-filled with substance to be dosed, wherein preferably the two ends of the tubes are sealed with a foil. The tubes can for example be purchased pre-filled and/or be stored pre-filled and then if required be received by the device according to the invention and be emptied.

With advantage at least some of the substance compartments have an inner surface with an arithmetic mean roughness value $R_a$ larger than 0.5 µm. Thus the intaken substance is held well.

In the case of an advantageous embodiment the device according to the invention comprises various classes of substance compartments with inner surfaces with different arithmetic mean roughness values $R_a$. Since the inner surfaces of the substance compartments of different classes have different arithmetic mean roughness values $R_a$, the classes of substance compartments concerned retain different quantities of substance. This enables a rapider approximation of the desired dosage quantity.

Preferably at least some of the substance compartments have on their inner surface flexible lamellae and/or barbs. Thereby the substance to be dosed is better retained in the substance compartment.

In the case of an advantageous embodiment, the device according to the invention comprises various classes of substance compartments with inner surfaces with different wettability. Thereby capillary forces can be optimally capitalized on and the concerned substance compartments of different classes can retain different quantities of fluid substance, which enables a rapider approximation of the desired dosage quantity.

With advantage the substance intake portion is automatically removable from the emptying portion, for example through pulling off at a fixed part. Substance intake portions can thus be automatically exchanged, for example with a change of substance and if need be are also designed cost effectively for one time usage, whereby the danger of impurities from other substances to be dosed can be ruled out.

Preferably the substance compartments are individually mounted in the substance intake portion and their number is variable. Thus as many substance compartments in a class can be mounted as precisely needed.

Preferably the substance compartments in the substance intake portion are individually displaceably mounted between a fill position, in which they are fillable, and an inactive position, in which they are not fillable. Therefore, as many substance compartments of a class can be brought into the fill position as precisely needed. The displaceability of the substance compartments can for example be guaranteed by their position in pipes, from which they can be moved out.

Advantageously the device according to the invention comprises means for vertical displacement of the substance intake portion. This enables the dipping in or insertion of the substance compartments in a simple way in the substance to be intaken and the further taking out of the substance compartments.

In the case of a preferred embodiment the emptying portion comprises means for the admission of pressure gas into every individual substance compartment. A pneumatic or another pressure surge can be produced for example by opening a valve, irreversible destruction of a component provided therefor or by emptying a pressure container. By the admission of pressure gas, a substance compartment can be emptied in a simple manner.

In the case of an alternative advantageous embodiment, for every substance compartment the emptying portion has a displaceable piston. With this piston the substance can then be expelled out of the substance compartment. Another mechanical component can also be used instead of a piston. The displacement of the piston or other mechanical component can be brought about for example by motors, springs, magnets or piezo elements.

In the case of another alternative embodiment the emptying portion has means for the alteration of the geometry of every individual substance compartment, which preferably comprise means for the production of a mechanical pressure, a voltage or a temperature change. The means for production of a mechanical pressure comprise for example piezo elements, in particular piezo ceramic composite elements. Through the change of geometry, the intaken substance can be released from the substance compartment and this can thus be emptied.

In the case of yet another alternative embodiment, the emptying portion has means for the alteration of the surface properties of the inner surface of every individual substance compartment, which preferably comprise means for the production of a voltage and/or a temperature change. By the alteration of the surface properties, the intaken substance can be released from the substance compartment and this can thus be emptied.

In the case of a further alternative embodiment, the emptying portion has means for the alteration of the flow properties of the substance to be dosed in every individual substance compartment, which preferably comprise means for the production a voltage or a temperature change. By the alteration of the flow properties of the substance to be dosed, the intaken substance can be released from the substance compartment and this can thus be emptied.

Advantageously the emptying portion and the substance intake portion are arranged on the weighing balance, such that they are weighed by this weighing balance. The arrangement of the emptying portion and the substance intake portion takes place for example as described in WO 02/29369 A1 for a customary dosing device. By this weighing from above, the amount of substance that is dispensed by the emptying of a substance compartment can be determined. The device according to the invention is so much more independent of location than in the case of the presence of a weighing balance beneath the vessel to be filled with substance. For example dosing can occur in the entire operating range of a robotic arm.

Alternatively to weighing from above, also only the dosing device can be arranged above the vessel to be filled, if this stands on a weighing balance.

It is also possible to work with two weighing balances: on one the dosing system is attached, a second stands under the vessel to be filled, for the control of the upper weighing balance.

Alternatively, the weighing balance, or a second weighing balance, is designed in order to receive a vessel to be filled and to measure the weight of the vessel and the substance dosed into the vessel. An advantage of this alternative is the fact that the weight of the already dosed substance, and not only the weight of the expelled substance is measured, which rules out a source of error. In case two weighing balances are used, advantageously at least one equally precise is used underneath. The second weighing balance can thereby directly measure the target vessel to be filled or an intermediate container, in which the substance is pre-dosed.

The method according to the invention for dosage of substances with a device according to the invention consists essentially of:

a) by emptying at least one substance compartment of a substance intake portion containing substance, substance is dosed into a vessel;
b) the quantity of dosed substance is determined with a weighing balance;
c) by control means it is calculated whether, and if need be, how much substance is still to be dosed into the vessel, and according to result, it is proceeded further with step a) or the dosage is ended.

This method enables a stepwise approximation of the desired dosage, that can take place completely automatically. An especial skill of the operator is not necessary.

With advantage the substance intake portion comprises substance compartments of various size classes and firstly, of the largest possible size class, the greatest number of substance compartments are emptied in which it is still certain that the desired dosage quantity is not overshot, then, of the next smaller size class, the greatest number of substance compartments in which it is still certain that the desired dosage quantity is not overshot are emptied, etc. until the desired dosage quantity with the desired precision is achieved. This enables a rapider approximation of the desired dosage quantity.

Preferably the quantity of dosed substance is determined after every emptying of a substance compartment. After every emptying with subsequent weight measurement, the situation can then be newly estimated, due to more exact numbers.

Alternatively, the quantity of dosed substance is determined only after the emptying of several substance compartments. Time can be saved in this manner.

In the case of a preferred embodiment, the substance compartments are tubes, which are filled before step a) by dipping in or insertion in substance which is found in a supply container, and then afterwards taken out of the substance again. In such a simple manner and in an automated way, substance can be taken in by the substance compartments.

With advantage, the weighing balance measures the weight loaded on it before and after filling the tubes, and the control means calculates from this, and from the known geometry of the individual tubes, the approximate quantity of substance in each tube. Then based on these numbers, the dosage can immediately begin.

Advantageously after the first, preferably after every, emptying of a tube of a size class, the approximate quantity of substance in a tube of this size class is newly estimated. This calibration enables a more precise determination of the substance quantity in a tube of a certain size class.

In the case of an advantageous embodiment, after filling of the tubes, firstly at least one tube of each size class is emptied and by generation of the weight difference before and after the emptying of each tube, the approximate quantity of substance in a tube of this size class is determined. Such a calibration also enables a more precise determination of the substance quantity in a tube of a certain size class.

Preferably, dosing firstly takes place in an intermediate container and when the desired dosage quantity with the desired precision is achieved, the intermediate container is emptied into the vessel; whereas if the desired dosage quantity with regard to the desired precision is overshot, the intermediate container is emptied again and the dosage is begun again. An overdosage can thus also be avoided with very small weight tolerances.

In the case of an advantageous embodiment, the actual dosage quantity in the intermediate container is determined by a second weighing balance, on which the intermediate container is fixed. The precision of dosage can thus be increased.

In the case of an advantageous embodiment with n same substance compartments, the weight G of the total intaken substance is determined by weighing, and from the number of the substance compartments n, the mass g per substance compartment is calculated:

$$g = G/n \qquad (1)$$

In the case of an advantageous embodiment, the substance compartments are graduated in size classes, the substance compartments within the same size class having the same volume, so that by the choice of a few substance compartments of various size classes, the entire dosage range can be covered. The volumes of the substance compartments of the various size classes are in a known ratio to each other. Each of the i size classes comprises $n_i$ equally sized substance compartments. In this case the calculation of the intaken substance per substance compartment is carried out according to Formula (2), in which the ratio of the volume of the individual substance compartment to the total volume is considered. The weight of the substance in a substance compartment of the size class i is $g_i$, the volume ratio is expressed by the contribution $v_i / \Sigma(n_i \cdot v_i)$:

$$g_i = \frac{G \cdot v_i}{\sum_{i=1}^{n}(n_i \cdot v_i)} \qquad (2)$$

As well it must be pointed out that the expressions "volume" and "volume ratios" always relate to the intaken substance or the substance to be intaken, and not to the empty substance compartments. Notably, these meanings apply for the entire patent application. With a cross section which is uniform in the vertical, the volume ratios of the empty substance compartments are the same among each other as those of the intaken substance. In the case of a varying cross section, the corresponding ratios of the geometric form must be correspondingly calculated.

The substance compartments filled with substance are brought over the vessel to be filled and the substance compartments are individually (singly or multiplely or all at the same time) or in their entirety emptied from above by ejection of the intaken substance.

A second aspect of the invention consists in the method for dosage of substances that is possible with the dosing device according to the invention.

The user firstly establishes a target range about the desired value, within which the achieved value must lie. He also does this in the classical manual method consciously or unconsciously. The smallest possible target range corresponds to the mass of the substance to be dosed in a substance compartment of the smallest size class.

If the substance intake portion and the emptying portion are attached on a weighing balance lying above, the total weight of the intaken substance is thus known from the total weight and the known empty weight of the substance intake portion and the emptying portion. Since the volume ratios and the number of the substance compartments are also known, the average fill weight per substance compartment for each size class can be calculated according to Formula 2, wherein the individual fill quantities can absolutely have a significant variation. The control program can decide from the average fill weight, which size of substance compartment should in each case be dosed next, until the target range is reached through ever smaller additions, whereby after each addition weighing takes place, in order to confirm the actual dosed quantity of substance and to decide about the further additions.

EXAMPLE

| | |
|---|---|
| Substance intake portion and emptying portion empty: | 15.0000 g |
| Substance intake portion and emptying portion after substance intake: | 15.0064 g |
| Total intaken weight G: | 6.4 mg |
| To dose (desired value and target range): | 3.32 mg ± 0.01 mg |
| Calculation of the fill quantity per substance compartment: | |
| 1 size class with 10 substance compartments, volume of these substance compartments: | $v_1 = 0.1$ µl |
| 3 size classes each with 4 substance compartments, volumes of the substance compartments of these size classes | $v_2 = 1$ µl, $v_3 = 3$ µl, $v_4 = 9$ µl |

For the various size classes the following average fill quantities to be expected are calculated according to Formula 2:

$$g_1 = G \cdot v_1 / \Sigma(n_i \cdot v_i) = 6.4 \text{ mg} \cdot 0.1 \text{ µl}/[(10 \cdot 0.1 \text{ µl}) + (4 \cdot 1 \text{ µl}) + (4 \cdot 3 \text{ µl}) + (4 \cdot 9 \text{ µl})] = 0.0121 \text{ mg}$$

$$g_2 = G \cdot v_2 / \Sigma(n_i \cdot v_i) = 6.4 \text{ mg} \cdot 1 \text{ µl}/[(10 \cdot 0.1 \text{ µl}) + (4 \cdot 1 \text{ µl}) + (4 \cdot 3 \text{ µl}) + (4 \cdot 9 \text{ µl})] = 0.121 \text{ mg}$$

$$g_3 = G \cdot v_3 / \Sigma(n_i \cdot v_i) = 6.4 \text{ mg} \cdot 3 \text{ µl}/[(10 \cdot 0.1 \text{ µl}) + (4 \cdot 1 \text{ µl}) + (4 \cdot 3 \text{ µl}) + (4 \cdot 9 \text{ µl})] = 0.362 \text{ mg}$$

$$g_4 = G \cdot v_4 / \Sigma(n_i \cdot v_i) = 6.4 \text{ mg} \cdot 9 \text{ µl}/[(10 \cdot 0.1 \text{ µl}) + (4 \cdot 1 \text{ µl}) + (4 \cdot 3 \text{ µl}) + (4 \cdot 9 \text{ µl})] = 1.09 \text{ mg}$$

It is then dosed according to the following Table:

| Addition | Calculated next addition in mg | Measurement of the accumulated additions in mg | Actual last addition in mg | Decision about next action: |
|---|---|---|---|---|
| 0 | 0 | 0 | 0 | Addition large |
| 1 | 1.09 | 1.003 | 1.003 | Addition large |
| 2 | 1.09 | 2.385 | 1.382 | Addition medium |
| 3 | 0.362 | 2.679 | 0.294 | Addition medium |
| 4 | 0.362 | 3.152 | 0.473 | Addition small |
| 5 | 0.121 | 3.281 | 0.129 | Addition finest |
| 6 | 0.0121 | 3.291 | 0.0099 | Addition finest |
| 7 | 0.0121 | 3.304 | 0.0133 | Addition finest |
| 8 | 0.0121 | 3.317 | 0.0125 | End |

The actual last addition is in each case either calculated on the basis of the previous addition or measured with a second weighing balance.

It is advantageous to always continue to work with the measured accumulated value, not with the calculated sum of the individual additions, so that unavoidable weighing mistakes are not accumulated.

Alternatively to this (for example if only a lower weighing balance is used and thus the total intaken weight is not known, or in order to save time) the average expelled substance quantity per size class can be determined at the beginning of the dosing process by the emptying of several substance compartments with weighing following in each case, i.e. a calibration is undertaken. This can take place directly in the vessel to be filled. With very small substance quantities to be dosed this step can take place in a waste vessel. Since through this the average substance quantity added per size class is known, afterwards by emptying several substance compartments of suitable size at the same time, dosage can be performed very quickly until a threshold value underneath the lower limit of the target range, i.e. a rough dosage is carried out. In the subsequent fine dosage the control program decides in turn which size of substance compartment is dosed in each case, until the target range is reached, whereby after each addition weighing is performed.

In the case of an advantageous embodiment, at a suitable time point during the dosage process, the actual average fill quantity and the statistical distribution of the substance quantity per size class is calculated from the previous addition and/or from the data of the calibration. The control program can then fit with this distribution the decision, of which size class is dosed next, with respect to the threshold value, until which such value the multiple substance compartments are emptied at the same time. Thus also with very unfavourable, i.e. wide distribution of the fill quantities, the target range is reliably achieved and an overdosing is avoided with a significantly higher probability.

BRIEF DESCRIPTION OF THE DRAWINGS

In the following, embodiments of the device according to the invention and the method according to the invention for dosage of substances are described in more detail with reference to the accompanying figures, in which:

FIG. 10—shows schematically the emptying of a substance compartment by a pneumatic pressure surge;

FIG. 11—shows schematically the emptying of a substance compartment by a pressure surge mechanically induced by means of a piston movement;

FIG. 12—shows schematically a part of an emptying portion and of a substance intake portion with a substance compartment filled with powdery substance;

FIG. 13—shows schematically the emptying of the substance compartment from FIG. 12 by alteration of its geometry by mechanical pressure;

FIG. 14—shows schematically the intake of a powdery substance by insertion of a substance compartment in substance present in a supply container;

FIG. 15—shows schematically the application of a tension for the alteration of the geometry of the substance compartment from FIG. 14 for the improvement of the intake of substance;

FIG. 16—shows schematically the emptying of the substance compartment from FIG. 15 by a change of the applied tension for the reversal of the geometrical alteration;

FIG. 17—shows schematically a part of an emptying portion and of a substance intake portion with a substance compartment filled with fluid substance;

FIG. 18—shows schematically the emptying of the substance compartment from FIG. 17 by alteration of the surface properties of the inner surface of the substance compartment by application of a voltage;

FIG. 19—shows schematically the first embodiment of the device according to the invention with a weighing balance, on which the emptying portion and the substance intake portion are fixed, arranged above a vessel to be filled;

FIG. 20—shows schematically a third embodiment of the device according to the invention with a weighing balance arranged below a vessel to be filled;

FIG. 21—shows schematically a fourth embodiment of the device according to the invention with a first weighing balance, on which the emptying portion and the substance intake portion are fixed, arranged above a vessel to be filled and a second weighing balance arranged below the vessel to be filled;

FIG. 22—shows a flow diagram of an embodiment of the method according to the invention for dosage of substances.

DETAILED DESCRIPTION

Figure 1:
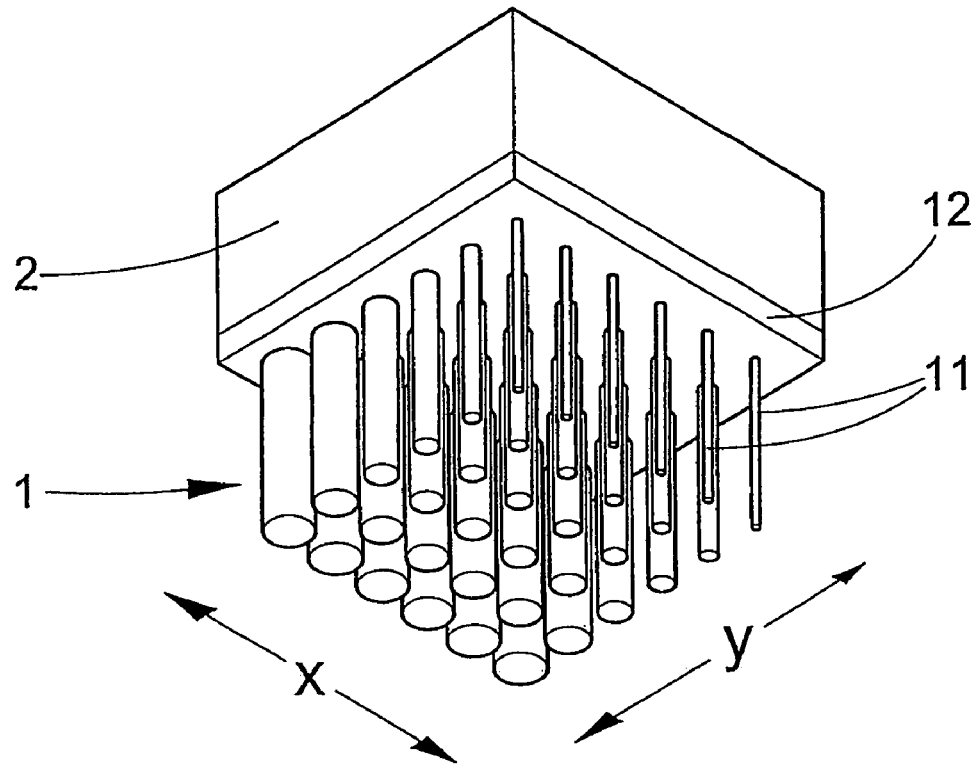
FIG. 1—shows a perspective view of a substance intake portion and of an emptying portion of a first embodiment of the device according to the invention for dosage of substances.
Figure 2:
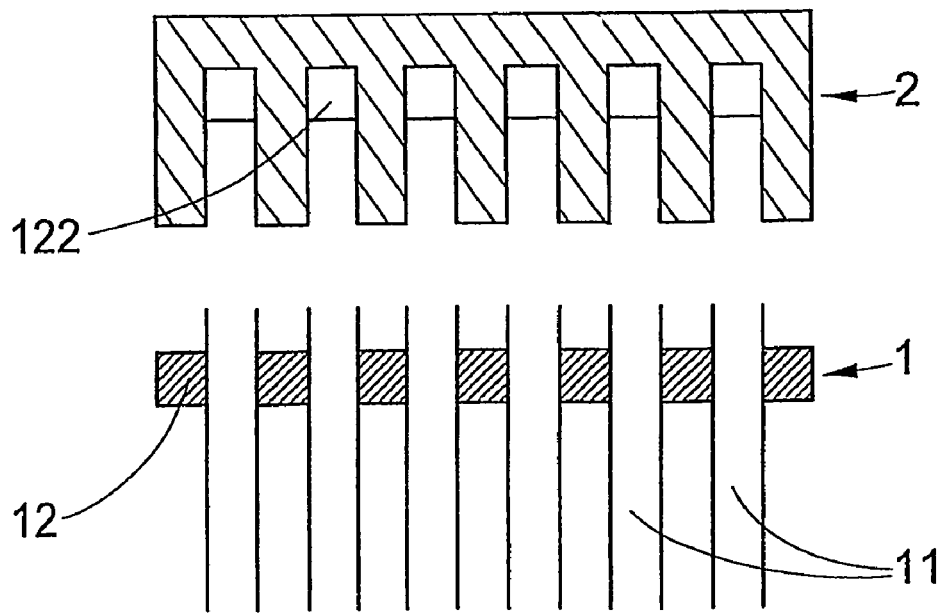
FIG. 2—shows a schematic section view of the device from FIG. 1 with substance intake portion separated from the emptying portion.

The part of a first embodiment presented in FIGS. 1 and 2 of the device according to the invention for dosage of substances comprises a substance intake portion 1 with a carrier plate 12, for example made out of plastic, on which a plurality of substance compartments in the form of tubes 11 are attached, which for example are made out of glass, plastic or metal. Of the tubes 11 which are open above and below, six tubes are present in each of six size classes. The tubes 11 of a size class have the same inner diameter and are arranged next to each other in the x-direction. In the y-direction the inner diameters of the tubes 11 decrease in terms of size class. Due to the varying inner diameters, the tubes 11 of different size classes normally take in different quantities of substances to be dosed.

The substance intake portion 1 is detachably fixed via the carrier plate 12 to an emptying portion 2. The emptying portion 2 has an emptying mechanism with which the tubes 11 can be individually emptied. In FIG. 2 pistons 122 which are movable in the vertical direction are observable. The pistons 122 are pushed into the tubes 11 and thereby the substance in the tubes 11 concerned is pressed out. Each tube 11 is associated with a piston 122. Each piston 122 is individually activatable, wherein customary driving systems can be used.

The substance intake portion 1 and the emptying portion 2 are preferably arranged on a displaceable robotic arm, which is not shown. Likewise not shown here is the weighing balance belonging to the device, which is further detailed below.

The following applies to the rest of this description. If, in order to clarify the drawings, a figure contains designations which are not explained in the directly associated text of the description, or vice versa, then you are referred to the point at which they have been mentioned in previous descriptions of the figures.

Figure 3:
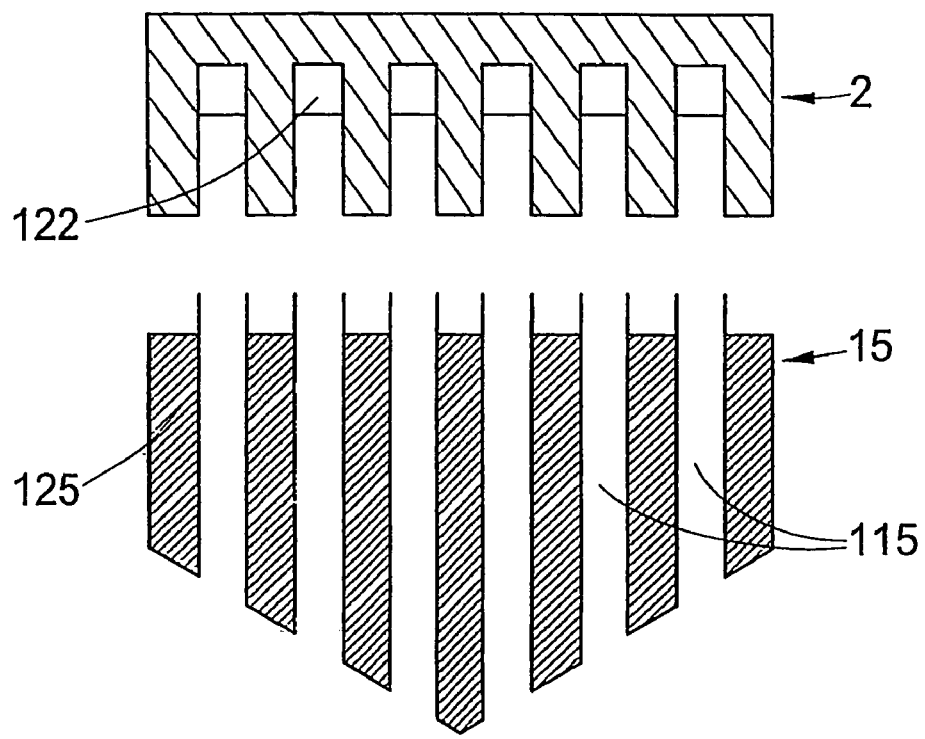
FIG. 3—shows a schematic section view of the substance intake portion and emptying portion which are separated from each other of a second embodiment of the device according to the invention.

FIG. 3 shows the substance intake portion 15 and the emptying portion 2 of a second embodiment of the device according to the invention, wherein the emptying portion 2 with the pistons 122 corresponds to that of the first embodiment. However, the substance intake portion 15 comprises a substance plate 125, for example made out of plastic or metal, into which substance compartments 115 are bored. In the lower section in the middle the substance plate 125 is pointed, which enables a simpler dipping in or insertion into the substance to be dosed. In addition it is lighter and cheaper to produce than the substance intake portion 1 according to the first embodiment.

Figure 4:
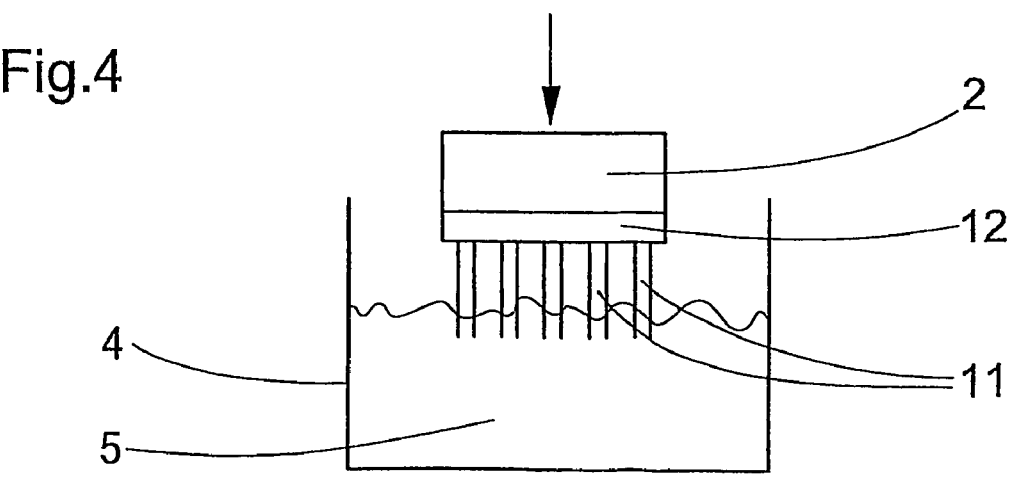
FIG. 4—shows schematically the intake of powdery substance by the substance intake portion of FIG. 1 by insertion into substance present in a supply container.

FIG. 4 shows the intake of powdery substance by the tubes 11 of the substance intake portion 1 by insertion in substance 5, which is present in a supply container 4. The vertical arrow indicates the vertical displacement of the substance intake portion 1 which is connected with the emptying portion 2, for insertion of the tubes 11 in the substance 5. After the insertion the tubes 11 are taken out of the substance 5 again, wherein then due to frictional forces, different quantities of substance 5 remain adhered in the tubes 11, according to the inner diameter of the tubes 11.

Figure 5:
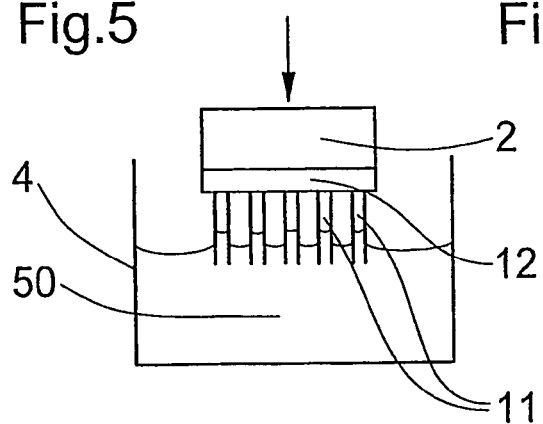
FIG. 5—shows schematically the intake of fluid substance by the substance intake portion from FIG. 1 by dipping into substance present in a supply container.

FIG. 5 shows the intake of fluid substance by the tubes 11 of the substance intake portion 1 by dipping in fluid substance 50, which is present in the supply container 4. The vertical arrow indicates the vertical displacement of the substance intake portion 1 which is connected with the emptying portion 2, for the dipping in of the tubes 11 in the substance 50. After the dipping in, the tubes 11 are taken out of the substance 50 again, wherein then due to capillary forces, different quantities of substance 50 remain adhered in the tubes 11, according to the inner diameter of the tubes 11.

Figure 6:
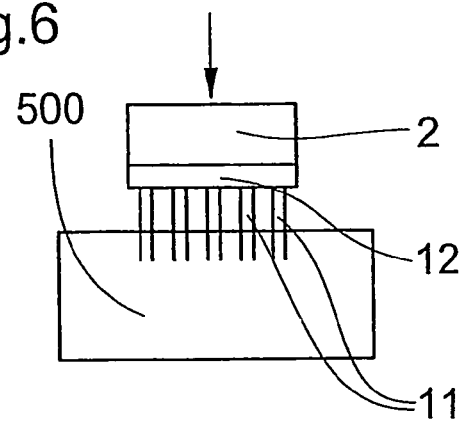
FIG. 6—shows schematically the intake of solid substance by the substance intake portion from FIG. 1 by insertion into a solid body.

FIG. 6 shows the intake of solid substance by the tubes 11 of the substance intake portion 1 by insertion in a solid body 500. The solid body 500 can be made out of almost any material that permits an insertion of the tubes 11, for example from polymer material, a wax disc or an apple. The vertical arrow indicates the vertical displacement of the substance intake portion 1 which is connected with the emptying portion 2, for insertion of the tubes 11 in the solid body 500. After the insertion the tubes 11 are taken out of the solid body 500 again, wherein then due to frictional forces, different quantities of solid substance 500 remain adhered in the tubes 11, according to the inner diameter of the tubes 11.

Figure 7:
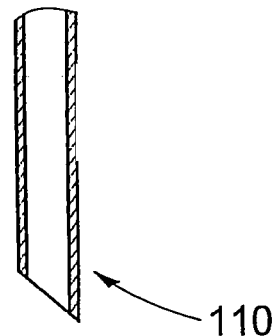
FIG. 7—shows a section view of the lower end of a substance compartment in the form of a tube which has a pointed lower section.
Figure 8:
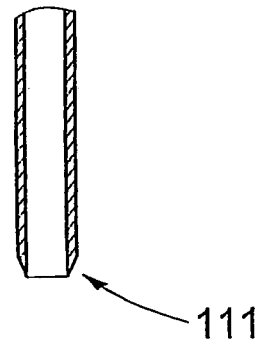
FIG. 8—shows a section view of the lower end of a substance compartment in the form of a tube which has a sharp-edged lower section.

In FIG. 7 the lower end of a substance compartment is presented in the form of a tube 110 which has a lower pointed section, while FIG. 8 shows the lower end of a substance compartment in the form of a tube 111 which has a lower sharp-edged section. These special designs of the lower ends of the tubes 110, 111 enable a simpler insertion in powdery or solid substances. With fluid substances these special ends lead to a more regular release of drops, i.e. to uniform actual dosage quantities of tubes 110, 111 of the same size class.

Figure 9:
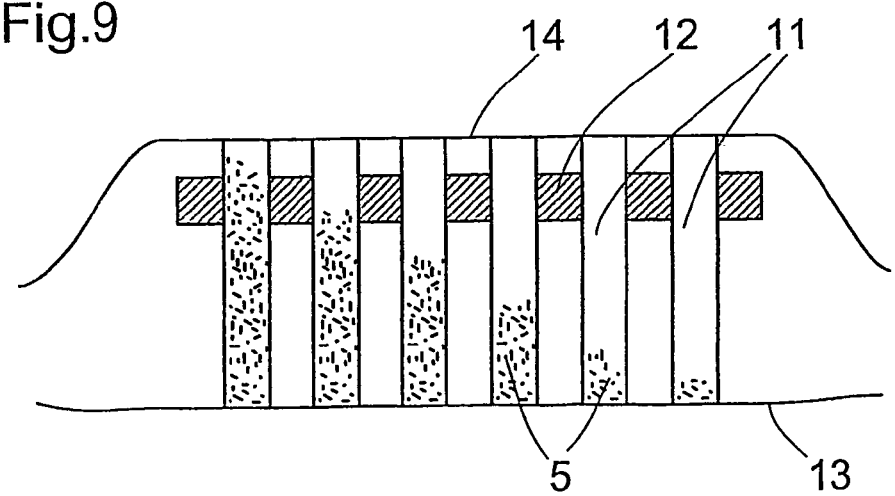
FIG. 9—shows a schematic section view of the substance intake portion from FIG. 1 with different pre-filled substance compartments which are sealed by foils.

The substance intake portion presented in FIG. 9 corresponds essentially to that of FIG. 1, however the tubes 11 are already pre-filled with varying quantities of substance 5 in regards to size classes. The tubes 11 are sealed above and below by foils 14 or 13, such that the substance intake portion can be transported and stored without problem, so that substance 5 is not lost or contaminated. The foils 13, 14 can be entirely peeled off immediately before use, or alternatively they can be destroyed when emptying the substance compartments 11, wherein preferably such foils 13, 14 are used that can be ripped so that no remains of the foil fall in the vessels to be filled.

In the case of the embodiment presented in FIG. 10 the emptying of a tube 11 takes place by a pneumatic pressure surge. For this nitrogen under pressure is let into the tube 11 via a gas line 22, which leads to a pressure surge, which expels out below the tubes 11 the intaken substance 5. The nitrogen comes for example out of a nitrogen container (not shown) and its admission into the tubes 11 is started by opening a valve 23 arranged in the gas line 22.

In the case of the embodiment presented in FIG. 11 the emptying of a tube 11 takes place by a mechanically induced pressure surge. The emptying portion 102 has for this a cylinder plate 121, which is provided with a plurality of vertically cylindrical bores, into which a piston 122 is vertically displaceable in each case. A piston 122 is present per tube 11, wherein the pistons 122 are individually movable independently from each other, by means of customary drives.

In the case of the embodiment presented in FIGS. 12 and 13, a tube 211 of a substance intake portion 201 is filled with powdery substance 5. The tube 211 has flexible walls, the geometry of which can be changed by exertion of a mechanical pressure. For the exertion of a mechanical pressure on the tube 211, the emptying portion 202, on which the substance intake portion 201 is fixed via a carrier plate 212, has pressure elements 222 in bores in a base plate 221, for example piezo elements, in particular piezo ceramic composite elements. In the present case, the tube 211 is enlarged below by exertion of a mechanical pressure on its upper part, which leads to a release of the intaken substance 5, and thus to the emptying of the tube 211.

The FIGS. 14 and 15 show the intake of a powdery substance 5 by insertion of a tube 330 of a substance intake portion in the substance 5 present in the supply container 4. After the insertion in the substance 5, the lower part of the tube 330, that has at least in its lower part flexible walls, is narrowed by application of a voltage in its upper part, whereby the substance 5 present in the tube 330 is compacted and wedged in. The application of the voltage takes place by means of an emptying portion, on which the substance intake portion is fixed via a carrier plate 312. The emptying portion has for this voltage electrodes 331 and 332, which are positioned in a base plate 321 in such a way that they are able to be brought into contact with the tube 330. So that the geometry of the lower part of the tube 330 changes due to the application of a voltage in the upper part, on the lower part, for example, piezo elements, in particular piezo ceramic composite elements, are attached, which are in electrical conducting connection with the regions of the tube 330 on which the voltage is applied.

After the tube 330 is taken out from the supply container 4 it can be fed from above into a vessel 6, into which the substance is to be dosed, for example by means of a robotic arm, on which the emptying portion and the substance intake portion can be attached. As presented in FIG. 16, the polarity of the applied voltage is then reversed, which with suitable design of the tube 330 and the piezo elements, leads to an expansion of the lower part of the tube 330 and to an emptying of the tube 330.

In the case of the embodiment presented in FIGS. 17 and 18 the emptying portion 302 likewise has voltage electrodes 331 and 332, which are positioned in a base plate 321 in such a way that they are able to be brought into contact with a tube 311 containing fluid substance 50. The emptying portion 302 can, however, additionally or alternatively, also have tempering means 322, for example an electrical resistance heating, with which the temperature of the tube 311 can be changed. Also here the substance intake portion 301 containing the tube 311 is connected via the carrier plate 312 with the emptying portion 302.

Through application of a voltage with the voltage electrodes 331 and 332 and/or through alteration of the temperature of the tube 311, the surface properties of the inner surface of the tube 311 can be changed and in this way an emptying of the tube 311 can be initiated. So that the surface properties are changed in the desired sense, the inner surface of the tube 311 can be layered for example with a semi-conductor, which by the application of a voltage goes from an insulated condition into a conducting condition. Thereby the wettability of the inner surface of the tube 311 changes, which can initiate the emptying.

FIG. 19 shows schematically the first embodiment of the device according to the invention with a weighing balance 3, on which the emptying portion 2 and the substance intake portion 1 are attached via coupling elements 7, 8, arranged above a vessel 6 to be filled. The weighing balance 3 is built for example as described in WO 02/29369, which is explicitly referred to here, and the substance intake portion 1, emptying portion 2 and coupling elements 7, 8 can also be fixed in an equivalent manner.

FIG. 20 shows schematically a third embodiment of the device according to the invention with a weighing balance 503 which is arranged underneath the vessel 6 to be filled, that can be a conventional weighing balance.

In the case of the fourth embodiment of the device according to the invention, which is presented in FIG. 21, the first weighing balance 3, on which the emptying portion 2 and the substance intake portion 1 are attached via the coupling elements 7, 8, is arranged above the vessel 6 to be filled; while the second weighing balance 503 is arranged below the vessel 6 to be filled. Thus, the quantity of substance expelled from the substance intake portion 1, as well as also the quantity of substance accumulated in the vessel 6 can be measured.

FIG. 22 shows a flow diagram of an embodiment of the method according to the invention for dosage of substances. Firstly the desired value to be reached and, subject to the substance compartments available, the target range arising from the desired precision, are established (not shown in the flow diagram).

Afterwards a calibration K of the substance compartments of the, in this case, m different size classes takes place. For this purpose n substance compartments of a size class are emptied in succession, and after each emptying weighing will take place. From this the average substance quantity in a substance compartment of this size class can be calculated. All m size classes are calibrated in succession.

After the calibration K, a rough dosage G takes place. Firstly a threshold value, until which a rough dosage can take place without great danger of an overdosage, is calculated. After the calculation of the threshold value, the calculation of the additions of substance still required to reach the threshold value is performed. The calculated substance additions are then undertaken by emptying the corresponding number of substance compartments in the vessel to be filled.

In the following fine dosage F, the amount that was dosed in the vessel to be filled is firstly weighed. The measurement result is then compared with the target range. If the measurement result lies in the target range, the dosage is ended. If it lies underneath the target range, a further suitable substance compartment is emptied and further weighed etc. until the target range is finally reached.

Figure 23:
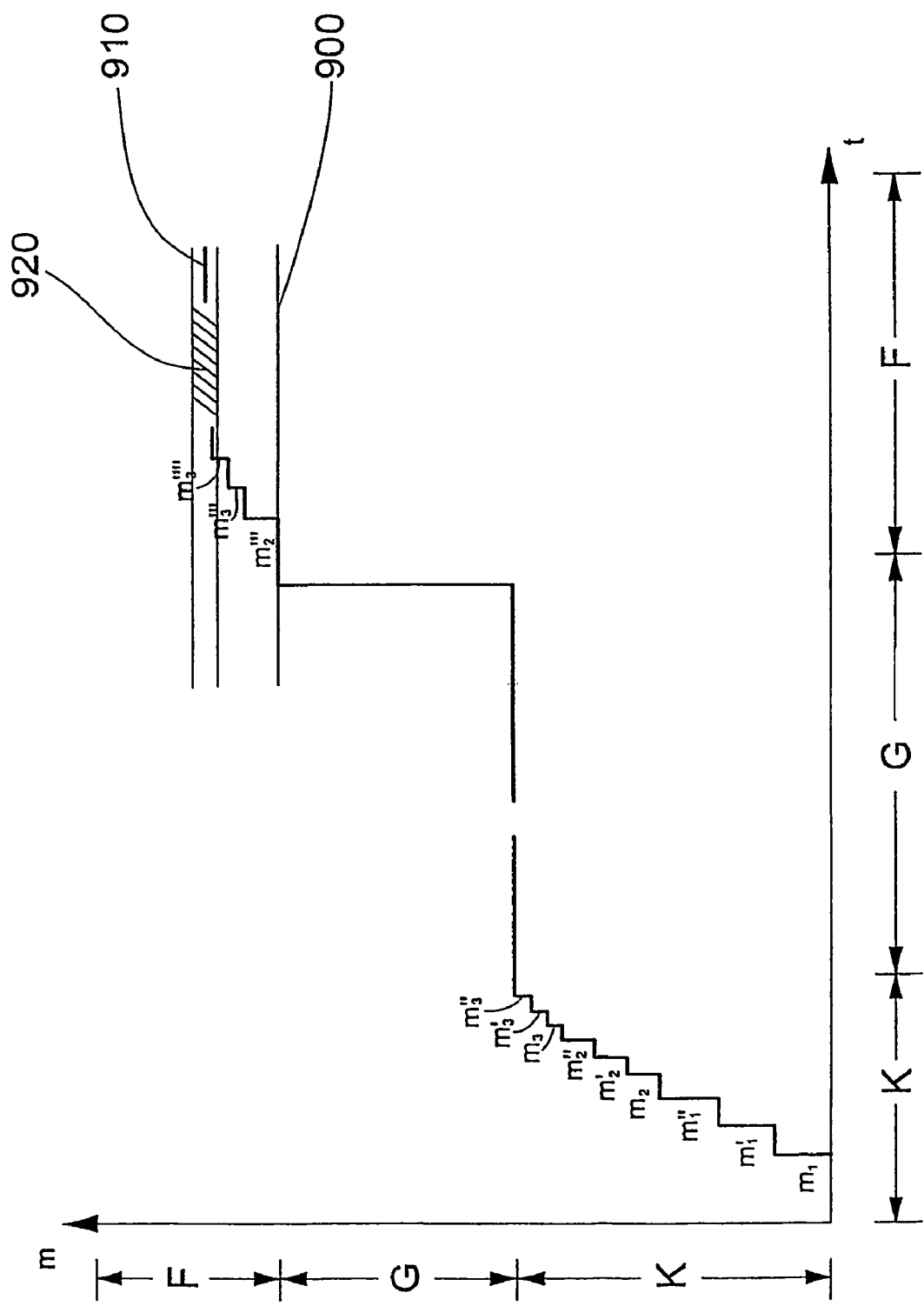
FIG. 23—shows a presentation of an example of the dosage of a substance with the method presented in FIG. 22.

In FIG. 23 an example of the dosage of a substance with the above-described method is presented. Firstly the desired value 910 and the target range 920 are established. Afterwards the m=3 various size classes of substance compartments are calibrated in succession, wherein for each size class, n=3 emptyings and weighings are performed. Then from this, for each size class, the average substance quantity in a substance compartment is calculated.

In the subsequent rough dosage G, the threshold value 900, until which a rough dosage can take place without great danger of an overdosage, is firstly calculated. After the calculation of the threshold value, the calculation of the additions of substance still required to reach the threshold value is performed and these are subsequently undertaken by emptying the corresponding number of substance compartments in the vessel to be filled.

Finally the fine dosage F takes place, in which the amount that was dosed in the vessel to be filled is firstly weighed. In the present case it was shown that the target range 920 was not yet reached and a substance compartment of the second size class was emptied, once again weighed, again compared with the target range 920, yet another substance compartment of the third size class was emptied, once again weighed, again compared with the target range 920, once again a substance compartment of the third size class was emptied, once again weighed and again compared with the target range 920. It could then be established that the measurement result lay in the target range, and the dosage could be ended.

Specific embodiments of a device for dosage of subtances according to the present invention have been described for the purpose of illustrating the manner in which the invention may be made and used. It should be understood that implementation of other variations and modifications of the invention and its various aspects will be apparent to those skilled in the art, and that the invention is not limited by the specific embodiments described. It is therefore contemplated to cover by the present invention any and all modifications, variations, or equivalents that fall within the true spirit and scope of the basic underlying principles disclosed and claimed herein.

What is claimed is:

1. A device for dosage of substances comprising:
   a substance intake portion, having a plurality of substance compartments for the intake of the substance to be dosed;
   an emptying portion for the complete emptying of at least one of the substance compartments each time in one step;
   a weighing balance for the determination of the quantity of dosed substance; and
   a control means for controlling the complete emptying of any one or more of the substance compartments each time in one step as needed dependent on the quantity of dosed substance as determined by means of the weighing balance.

2. The device according to claim 1, wherein the substance intake portion comprises substance compartments of various size classes, with which various quantities of substance to be dosed can be obtained.

3. The device according to claim 2, wherein at least some of the size classes are graduated across at least a factor of 5, preferably in the ratio 1:2:5.

4. The device according to claim 1, wherein at least some of the substance compartments are pre-filled with the substance to be dosed and preferably are sealed.

5. The device according to claim 1, wherein the substance compartments are formed as vertically arranged tubes.

6. The device according to claim 5, wherein the tubes of different size classes have different inner diameters.

7. The device according to claim 5 wherein the inner diameters of the tubes are smaller than 5 mm, preferably smaller than 1 mm, more preferably smaller than 0.5 mm, in particular preferably smaller than 0.1 mm.

8. The device according to claim 5, wherein at least some of the tubes narrow progressively from the top of the tube to the bottom of the tube.

9. The device according to claim 5, wherein at least some of the tubes have pointed or sharp-edged lower sections.

10. The device according to claim 5, wherein at least some of the tubes are pre-filled with the substance to be dosed and preferably the two ends of the tubes are sealed with foil.

11. The device according to claim 1 wherein at least some of the substance compartments have an inner surface with an arithmetic mean roughness value $R_a$ larger than 0.5 μm.

12. The device according to claim 1, further comprising various classes of substance compartments with inner surfaces with different arithmetic mean roughness values $R_a$.

13. The device according to claim 1, wherein at least some of the substance compartments have, on their inner surface, flexible lamellae and/or barbs.

14. The device according to claim 1, further comprising various classes of substance compartments with inner surfaces with different wettability.

15. The device according to claim 1, wherein the substance intake portion is automatically removable from the emptying portion.

16. The device according to claim 1, wherein the substance compartments are individually mounted in the substance intake portion and their number is variable.

17. The device according to claim 1, wherein the substance compartments in the substance intake portion are individually displaceably mounted between a fill position, in which they are fillable, and an inactive position, in which they are not fillable.

18. The device according to claim 1, further comprising means for vertical displacement of the substance intake portion.

19. The device according to claim 1, wherein the emptying portion comprises means for the admission of pressure gas into every individual substance compartments.

20. The device according to claim 1, wherein for every substance compartment the emptying portion has a displaceable piston.

21. The device according to claim 1 wherein the emptying portion has means for the alteration of the geometry of every individual substance compartment, which further comprise means for the production of a mechanical pressure, a voltage or a temperature change.

22. The device according to claim 1, wherein the emptying portion has means for the alteration of the surface properties of the inner surface of every individual substance compartment, which further comprise means for the production of a voltage and/or a temperature change.

23. The device according to claim 1 wherein the emptying portion has means for the alteration of the flow properties of the substance to be dosed in every individual substance compartment, which further comprise means for the production of a voltage or a temperature change.

24. The device according to claim 1, wherein the emptying portion and the substance intake portion are arranged on the weighing balance such that they are weighed by said weighing balance.

25. The device according to claim 1, wherein the weighing balance or a second weighing balance is designed in order to receive a vessel to be filled and to measure the weight of the vessel and the substance dosed into the vessel.

26. A method for dosage of substances with a device for dosage of substances having a substance intake portion, with a plurality of substance compartments for the intake of the substance to be dosed; an emptying portion for the complete emptying of at least one of the substance compartments each time in one step; a weighing balance for the determination of the quantity of dosed substance; and, a control means for controlling the complete emptying of any one or more of the substance compartments each time in one step as needed dependent on the quantity of dosed substance as determined by means of the weighing balance;

the method comprising:
a) completely emptying in one step at least one substance compartment of a substance intake portion containing a substance such that substance is dosed into a vessel;
b) determining the quantity of substance dosed in the vessel using a weighing balance; and
c) calculating with the control means whether, and if need be, how much additional substance must be dosed into the vessel, and according to the calculation result, either repeating steps a) to c) or stopping.

27. The method according to claim 26, wherein the substance intake portion comprises substance compartments of varying size classes, and starting with the greatest possible number of substance compartments of the largest possible size class being emptied into the vessel while it is still certain that the desired dosage quantity is not exceeded, then, proceeding with the greatest possible number of substance compartments of the next smaller size class being emptied into the vessel while it is still certain that the desired dosage quantity is not exceeded, and repeating until the desired dosage quantity with the desired precision is achieved.

28. The method according to claim 26, wherein the quantity of dosed substance is determined after every emptying of a substance compartment.

29. The method according to claim 26, wherein the quantity of dosed substance is determined only after the emptying of several substance compartments.

30. The method according to claim 26, wherein the substance compartments are filled before step a) by dipping them in or inserting them in substance which is found in a supply container, and then removing the compartments from the container.

31. The method according to claim 30, wherein the weighing balance measures the weight loaded on it before and after filling of the substance compartments, and the control means calculates from this, and from the known geometry of the individual substance compartments, the approximate quantity of substance in each substance compartment.

32. The method according to claim 30, wherein after every emptying of a substance compartment of a size class, the approximate quantity of substance in the remaining substance compartments of this size class is newly estimated.

33. The method according to claim 30, wherein after the filling of the substance compartments, at least one substance compartment of each size class is emptied and by calculation of the weight difference before and after the emptying of each substance compartment, the approximate quantity of substance in a substance compartment of this size class is determined.

34. The method according to claim 26, wherein dosing first takes place in an intermediate container, and when the desired dosage quantity with the desired precision is achieved, the intermediate container is emptied into the vessel; whereas if the desired dosage quantity with regard to the desired precision is exceeded, the intermediate container is emptied again and the dosage is begun again.

35. The method according to claim 34, wherein the actual dosage quantity in the intermediate container is determined by a second weighing balance on which the intermediate container is arranged for measurement.

* * * * *